United States Patent [19]

Mosley

[11] Patent Number: 4,845,796
[45] Date of Patent: Jul. 11, 1989

[54] ROTATING FLEXIBLE STEM TOOTH BRUSH

[76] Inventor: Randy Mosley, Rte. 1, Box 111, Lucasville, Ohio 45648

[21] Appl. No.: 77,651

[22] Filed: Jul. 24, 1987

[51] Int. Cl.⁴ .................. A46B 13/02; A46B 15/00
[52] U.S. Cl. .............................. 15/23; 15/105; 362/91
[58] Field of Search .................. 15/22 R, 23, 24, 28, 15/29, 167, 105; 362/91, 119

[56] References Cited

U.S. PATENT DOCUMENTS

| | | | |
|---|---|---|---|
| 2,314,117 | 3/1943 | Beckner | 15/23 |
| 2,618,003 | 11/1952 | Robey | 15/184 X |
| 2,778,043 | 1/1957 | Arf | 15/28 |
| 3,407,431 | 10/1968 | Melnik | 15/23 |
| 3,451,086 | 6/1969 | Burgett | 15/23 |
| 3,800,350 | 4/1974 | Francolino | 15/23 |
| 3,890,984 | 6/1975 | Lesetar | 15/23 X |
| 3,987,549 | 10/1976 | Robertelli | 15/23 X |
| 4,275,749 | 6/1981 | Caroli | 15/23 X |

FOREIGN PATENT DOCUMENTS

| | | | |
|---|---|---|---|
| 3332247 | 3/1985 | Fed. Rep. of Germany | 15/23 |
| 1066990 | 1/1954 | France | 15/23 |
| 1133470 | 11/1956 | France | 15/23 |
| 2575375 | 7/1986 | France | 15/105 |
| 512380 | 1/1955 | Italy | 15/24 |
| 517958 | 3/1955 | Italy | 15/105 |
| 2080099 | 2/1982 | United Kingdom | 15/23 |

*Primary Examiner*—Edward L. Roberts
*Attorney, Agent, or Firm*—Richard L. Miller

[57] ABSTRACT

This tooth brush is designed to effectively clean a person's teeth by rotation. Primarily, it consists of an electric motor in a housing that is hand held, and a flexible brush stem is received in the shaft of the motor and includes bristles that are radially disposed on the other end of the flexible brush stem.

1 Claim, 1 Drawing Sheet

U.S. Patent    Jul. 11, 1989    4,845,796
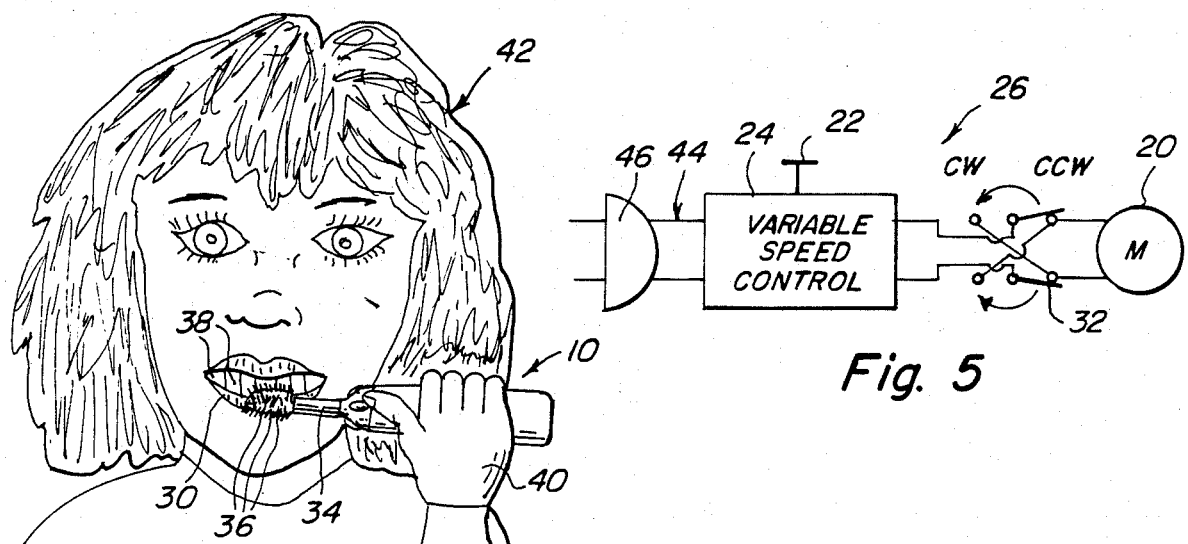
Fig. 1
Fig. 5
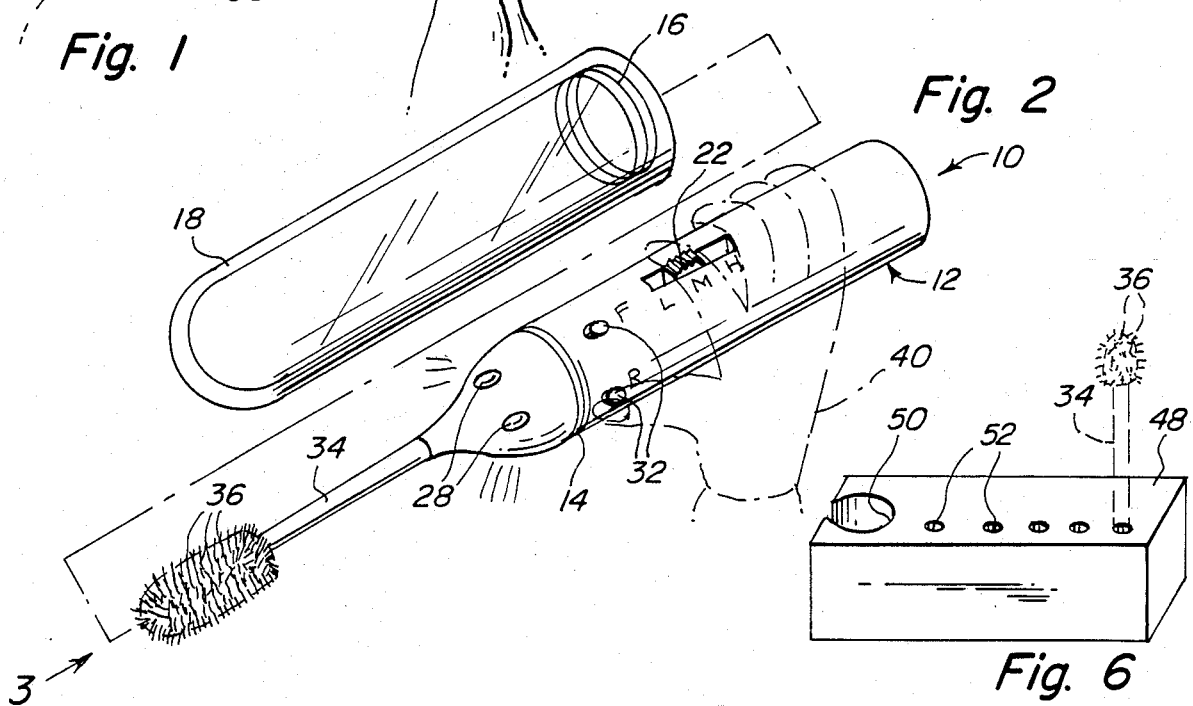
Fig. 2
Fig. 6
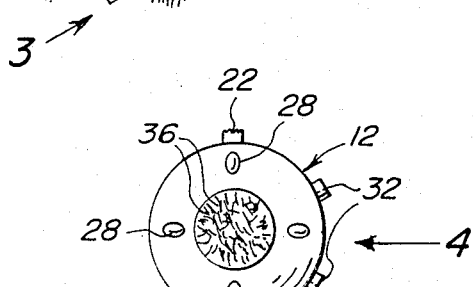
Fig. 3
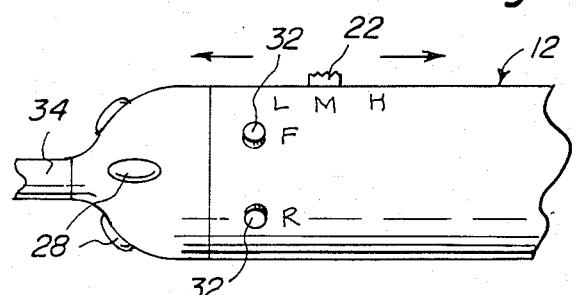
Fig. 4

ROTATING FLEXIBLE STEM TOOTH BRUSH

BACKGROUND OF THE INVENTION

The instant invention relates generally to oral devices, and more particularly, to a rotating flexible stem tooth brush.

Numerous tooth brushes have been provided in the prior art that are adapted to be electrically operated. While these units may be suitable for the particular purpose to which they address, they would not be as suitable for the purpose of the present invention as hereafter described.

SUMMARY OF THE INVENTION

A primary object of the present invention is to provide a rotating flexible stem tooth brush that will overcome the shortcomings of the prior art devices.

Another object is to provide a rotating flexible stem tooth brush, which will be of such design, as to more effectively clean a person's teeth.

An additional object is to provide a rotating flexible stem tooth brush, which will have three speed operation and may be counter rotated when desired.

A further object is to provide a rotating flexible stem tooth brush that is simple and easy to use.

A still further object is to provide a rotating flexible stem tooth brush that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 is a side view of the invention being used to brush the teeth of a person;

FIG. 2 is an enlarged perspective view of the invention;

FIG. 3 is an end view as indicated by arrow 3 in FIG. 2;

FIG. 4 is a side view as indicated by arrow 4 in FIG. 3 with parts broken away;

FIG. 5 is a electrical schematic diagram of the invention;

FIG. 6 is a perspective view of a typical stand for holding the attachments.

DETAILED DESCRIPTION OF THE PREFERRED EMBODIMENTS

Turning now descriptively to the drawings, in which like reference characters denote like elements throughout the several views, a tooth brush 10 is shown to include a housing 12 having threads 14 externally on the forward portion thereof, for engaging internal threads 16 on the open portion of a clear plastic cover 18. An electric motor 20 is secured on the interior of housing 12 and a switch 22 in a variable speed control unit 24, is wired in the circuit 26 of motor 20, for regulating the speed of motor 20 from low and medium to high. Lights 28 are also provided in the forward portion of housing 12 and are wired into circuit 26 in a manner (not shown), for illuminating the area of the mouth 30.

Switches 32 are also provided in housing 12, for polarity reversing of motor 20 to change its direction of rotation, and a flexible stem 34 is provided with bristles 36 on one end that clean teeth 38. The other end of stem 34 is frictionally received in the shaft of motor 20 in housing 12, and a total of three stems 34 are provided for use in tooth brush 10. One is soft, another is medium, and the third is hard, for any selection desired.

The switches 32 for clock-wise rotation and counter clock-wise rotation of stem 34, provides for preventing food from being brushed up under the gums, and bristles 36 are designed to enable a user to get into hard to reach areas of the teeth 38.

Housing 12 is designed to be easily held in the hand 40 of the user 42 and the electric cord 44 includes a plug 46 for entry into an electrical outlet receptacle. However, it shall be recognized that the design of tooth brush 10 may be readily modified for the employment of batteries as a power source.

Referring now to FIG. 6 of the drawing, a stand 48 is provided with a vertical end opening 50 for the reception of tooth brush 10 and a plurality of spaced smaller openings 52 are also provided vertically in stand 48, for the reception of a plurality of stems 34, one being provided for each member of the family.

In operation, the housing 12 is held in hand 40 and plug 46 is pushed into a receptacle. A teeth cleaning agent is then put on the bristles 36 and is employed to clean teeth 38 after switch 22 is placed in the speed position desired.

Either direction of rotation of stem 34 effected by pushing a switch 32, and when desired, stem 34 is pulled out of the shaft of motor 20.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A rotating flexible stem tooth brush comprising, a housing, an electric motor secured in a circuit in said housing, switch means secured in said housing for control of said motor, a brush stem received in said housing and a shaft of said motor, and a cover received over said brush stem for preventing contamination, wherein said housing is externally threaded near a forward end and is threadingly received in said cover that is internally threaded and said brush stem is flexible and one end is frictionally received in said shaft of said motor, wherein another end of said brush stem is provided with a plurality of bristles that are radially spaced apart and extend a partial length of said brush stem for contact with teeth, wherein lamps are secured in said circuit and arranged circumferentially in said forward end of said housing around said brush stem and illuminates the area of said teeth and said bristles of said brush stem.

* * * * *